United States Patent
Bootman et al.

[11] Patent Number: 6,071,447
[45] Date of Patent: Jun. 6, 2000

[54] METHOD OF MAKING A POLYURETHANE-BIOPOLYMER COMPOSITE

[75] Inventors: Matthew Bootman, Medfield, Mass.; Ronald Yamamoto, San Francisco, Calif.

[73] Assignee: Integra LifeScineces I, Ltd., Plainsboro, N.J.

[21] Appl. No.: 08/947,189

[22] Filed: Oct. 8, 1997

Related U.S. Application Data

[63] Continuation of application No. 08/751,419, Nov. 18, 1996, abandoned, which is a continuation of application No. 08/058,510, May 4, 1993, abandoned, which is a continuation-in-part of application No. 07/539,990, Jun. 14, 1990, abandoned.

[51] Int. Cl.[7] .......................... A61K 31/74; A61K 47/48
[52] U.S. Cl. ...................... 264/54; 264/51; 264/331.19; 424/78.17
[58] Field of Search .............................. 264/330, 331.19, 264/53, 54, 51; 424/78.17; 604/265, 266

[56] References Cited

U.S. PATENT DOCUMENTS

| | | |
|---|---|---|
| 3,427,301 | 2/1969 | Needles . |
| 3,469,003 | 9/1969 | Hardy . |
| 3,914,402 | 10/1975 | Shell . |
| 4,001,388 | 1/1977 | Shell . |
| 4,061,787 | 12/1977 | Higgins . |
| 4,115,544 | 9/1978 | Shell . |
| 4,178,361 | 12/1979 | Cohen et al. ............................ 424/22 |
| 4,280,954 | 7/1981 | Yannas . |
| 4,381,380 | 4/1983 | Le Veen et al. ..................... 424/78.17 |

(List continued on next page.)

FOREIGN PATENT DOCUMENTS

| | | |
|---|---|---|
| 0 048 558 | 3/1982 | European Pat. Off. ........ A61L 15/03 |
| 0 224 987 | 6/1987 | European Pat. Off. ....... A61K 47/00 |
| 0283408 | 9/1988 | European Pat. Off. ............ 424/78.17 |
| 0 341 745 | 11/1989 | European Pat. Off. ........ C08B 15/00 |
| 0 161 043 | 11/1995 | European Pat. Off. ........ C08G 18/64 |
| 2748 882 | 5/1979 | Germany ........................ A61L 15/03 |
| 2047093A | 11/1980 | United Kingdom . |
| 2047094A | 11/1980 | United Kingdom . |
| 2108517A | 5/1983 | United Kingdom . |
| WO 84/01102 | 3/1984 | WIPO ............................ A61F 13/06 |
| WO 90/04429 | 5/1990 | WIPO ........................... A61M 25/02 |
| WO 90/05755 | 5/1990 | WIPO ............................ C08G 83/00 |

OTHER PUBLICATIONS

Weadock, R., "Evaluation of Collagen Crosslinking Techniques", *Biomat., Med. Dev, Arr. Org.*, 11(4), 293–318, (1983–84).

Chvapil, M., "Medical and Surgical Applications of Collagen", *Int. Rev. Conn. Tissues*, 6:1–61, 1973.

Ricard–Blum, S., "Collagen Cross–Linking", *Int. J. Biochem.*, vol. 21, No. 11, pp. 1185–1189, 1989.

Chvapil, M., "Effect of Tanning Agent on Tissue Reaction to Tissue Implanted Collagen Sponge" *Journal of Surgical Research* 35, 402–409 (1983).

Dunn, M., "Studies on Collagen Implants in the Vitreous", *Surgical Forum Ophthalmic Surgery*, vol. 19, pp. 492, (1968).

Rubin, A., "Collagen as a Biomaterial", *Technology Review*, Dec., 1968, vol. 71, No. 2, pp. 44 (45).

Balazas, E. "The Injection of Hyaluronic Acid and Reconstituted Vitreous in to the Vitreous Cavity", New and Controversial Aspects of Retinal Detachment, Hoeber Medical Division, Harper & Row pp. 371–376.

*Primary Examiner*—Allan R. Kuhns
*Attorney, Agent, or Firm*—Campbell & Flores LLP

[57] ABSTRACT

A method is provided for preparing a drug delivery material and device comprising cross-linking a biological polymer with a cross-linking agent and loading the cross-linked biopolymer with a bioactive agent. Preferred embodiments are disclosed wherein the drug delivery material is used in a catheter securing, drug delivery device, in a wound dressing, and in a wound dressing for percutaneous catheters.

17 Claims, 8 Drawing Sheets

U.S. PATENT DOCUMENTS

| | | |
|---|---|---|
| 4,404,033 | 9/1983 | Steffan . |
| 4,409,201 | 10/1983 | Heinrich et al. .......................... 424/32 |
| 4,432,964 | 2/1984 | Shell . |
| 4,448,718 | 5/1984 | Yannas . |
| 4,460,560 | 7/1984 | Tokes et al. ........................ 424/78.17 |
| 4,500,453 | 2/1985 | Shank . |
| 4,535,010 | 8/1985 | Axen . |
| 4,590,020 | 5/1986 | Itaba . |
| 4,591,496 | 5/1986 | Cohen et al. ............................ 424/15 |
| 4,650,674 | 3/1987 | Aggarwal et al. ........................ 424/85 |
| 4,692,336 | 9/1987 | Eckenhoff et al. .................... 424/468 |
| 4,703,108 | 10/1987 | Silver . |
| 4,814,182 | 3/1989 | Graham . |
| 4,847,049 | 7/1989 | Yamamoto ................................ 422/24 |
| 4,856,504 | 8/1989 | Yamamoto et al. ............... 128/92 ZW |
| 4,863,647 | 9/1989 | Baylor, Jr. . |
| 4,865,846 | 9/1989 | Kaufman . |
| 4,911,920 | 3/1990 | Jani . |
| 4,915,694 | 4/1990 | Yamamoto et al. .................... 604/180 |
| 4,915,947 | 4/1990 | Thenard et al. ....................... 424/408 |
| 4,958,008 | 9/1990 | Petite . |
| 4,970,298 | 11/1990 | Silver . |
| 4,971,954 | 11/1990 | Brodsky . |
| 4,981,912 | 1/1991 | Kurihara . |
| 5,024,742 | 6/1991 | Nesburn . |
| 5,041,292 | 8/1991 | Feijen . |
| 5,066,490 | 11/1991 | Neville, Jr. et al. ................. 424/85.91 |
| 5,091,176 | 2/1992 | Braatz et al. ....................... 424/78.17 |
| 5,093,126 | 3/1992 | Jani . |
| 5,252,494 | 10/1993 | Walt ........................................ 436/528 |
| 5,266,323 | 11/1993 | Guthrie et al. ...................... 424/78.17 |
| 5,807,581 | 9/1998 | Rosenblatt et al. .................... 424/484 |

METHOD OF MAKING A POLYURETHANE-BIOPOLYMER COMPOSITE

This application is a continuation of application Ser. No. 08/751,419, filed Nov. 18, 1996, now abandoned; which is a continuation of 08/058,510, filed May 4, 1993, now abandoned; which is a continuation-in-part of Ser. No. 07/539,990, filed Jun. 14, 1990, now abandoned.

The present invention is related to a polymeric delivery vehicle for delivery of bioactive agents, and in particular, for the delivery of antimicrobial agents. The invention is also directed to a catheter-securing and drug delivery device comprising, as a component thereof, a material which delivers antimicrobial and/or other wound-healing factors at the site of the insertion of the catheter into the body.

BACKGROUND OF THE INVENTION

Techniques have been developed for administering pharmaceuticals through the skin by absorption. Such techniques are accomplished by devices which typically comprise either a pharmaceutical-containing reservoir enclosed by a synthetic membrane through which the pharmaceutical can diffuse at a controlled rate, or a dispersion of a pharmaceutical in a synthetic polymer matrix in which the pharmaceutical can diffuse at a controlled rate. While such delivery devices work for some pharmaceuticals, the rate of release of other pharmaceuticals is not adequate through synthetic polymers. Either the rate of delivery is too slow to provide an effective dosage given the area of the delivery surface, or in some cases, where prolonged delivery of the drug is desired, delivery is too fast so that the device must be replaced within a short period of time. One situation in which it is desirable to have a drug delivered over a prolonged period of time without removal of the delivery device is the case of delivery of drugs at a wound site around a percutaneous medical device.

Moreover, it is desirable, particularly when dealing with delivery of bioactive agents which are natural products, such as growth factors, that the polymeric matrix from which the drug is delivered be tailored for optimal drug delivery rate. It is difficult to do this when the drug to be delivered is a biological macromolecule, such as an enzyme or surface receptor, since specialized binding functionalities with proper charge density, orientation, hydrophobic domains, etc. are not readily synthesized into synthetic polymers to release the biological macromolecule at a desired controlled rate.

It is thus an object of the present invention to provide a polymeric delivery compositions for controlled release of bioactive agents, particularly biological macromolecules, which is formed of a foam composite of a biopolymer and a synthetic polymer.

It is another object of the present invention to provide drug delivery devices, particularly wound dressings, containing such polymeric delivery vehicles for controlled release of antimicrobial and/or wound-healing agents to aid in the wound healing process.

It is another object of the present invention to provide a catheter-securing and drug delivery device which is easily used which contains a pad comprising a biopolymer which serves as a delivery vehicle for controlled release of a bioactive agent to the catheter wound site.

These and other objects of the invention will be apparent from the following description and appended claims, and from practice of the invention.

SUMMARY OF THE INVENTION

The present invention provides a method for preparing a polymeric delivery vehicle for controlled release of a bioactive agent. The method comprises the steps of cross-linking a biopolymer which contains chemically reactive functionalities which react with a cross-linking reagent, where the cross-linking agent comprises greater that two reactive sites per molecule which are chemically reactive with functionalities on the biopolymer, to form a cross-linked biopolymer; optionally, forming the cross-linked biopolymer into a desired shape; then contacting the cross-linked biopolymer with a bioactive agent to reversibly bind the bioactive agent to the biopolymer to form the polymeric delivery vehicle. Preferably, the cross-linking reagent is a polyurethane or polyurethane urea having isocyanate side groups and/or end groups. It will be appreciated that the number of reactive sites per molecule of the cross-linking agent is a statistical average, therefore some cross-linking molecules will contain two or less reactive sites. Alternatively, the bioactive agent is bound to the biopolymer before treatment with the cross-linking agent. By effective binding affinity it is meant that the bioactive agent can be bound (noncovalently) to sites in the biopolymer; then, when in use in contact with skin and/or bodily fluids, or other fluids, a substantial amount of the bioactive agent will be released from the biopolymer, with release sustained for a period of time, controlled by the binding affinity.

As used herein, the term "binding affinity" is the ratio of the amount of bound drug (the bioactive agent) to the amount of free drug, wherein

[Bound drug] =[the total amount of drug found in a biopolymer sample which is contacted with a solution of drug and allowed to equilibrate] minus [the volume of solution absorbed by the biopolymer times the concentration of drug in the remaining unabsorbed solution]

[Free drug] =[the total amount of drug found in the biopolymer sample] minus [Bound drug].

Thus, $$\text{Binding affinity} = \frac{[\text{Bound drug}]}{[\text{Free drug}]} = \frac{[\text{Bound drug}]}{[\text{Total drug}] - [\text{Bound drug}]}$$

Generally, a higher binding affinity provides a longer sustained release of drug. Particularly preferred compositions have binding affinities over 0.8, preferably 1.0 and higher. Useful compositions have a binding affinity for the drug in the range of 1.0 to 5.0.

In a preferred embodiment of the present invention, the polymeric delivery vehicle is used in a catheter-securing and drug delivery device. The device comprises an elastomeric pad having a radial slit extending from the edge of the pad to a central point proximate to the center of the pad. The pad comprises a cross-linked biopolymer and a bioactive reagent reversibly bound thereto, wherein the bioactive reagent is releasable from the cross-linked biopolymer in a controlled manner to a wound or to the skin. The device further comprises a reinforced, flexible, water vapor permeable membrane adhesively attached to the pad which extends beyond the edge of the pad on all sides thereof, thereby forming a flange surrounding the pad. At least the edges of the exposed bottom surface of the membrane is coated with an adhesive material for affixing the device to the skin. The membrane has another radial slit extending from the edge of the membrane, through the membrane toward the central point of the pad, which is colinearally aligned with the slit in the pad. Finally, the device optionally comprises a reinforced, flexible, water vapor permeable tab affixed to the upper surface of the membrane and located proximate to one side of the pad wherein one surface of the tab is adhesively coated and the tab has dimensions sufficient to cover the pad when the tab is folded for adhesive attachment to the upper surface of the pad.

In another preferred embodiment the polymeric delivery vehicle in the form of an elastomeric pad is used as a wound dressing. The pad may be secured upon a wound by an adhesive water-vapor film over the pad which adheres to the skin area surrounding the wound.

DETAILED DESCRIPTION OF THE INVENTION

Figure 1:
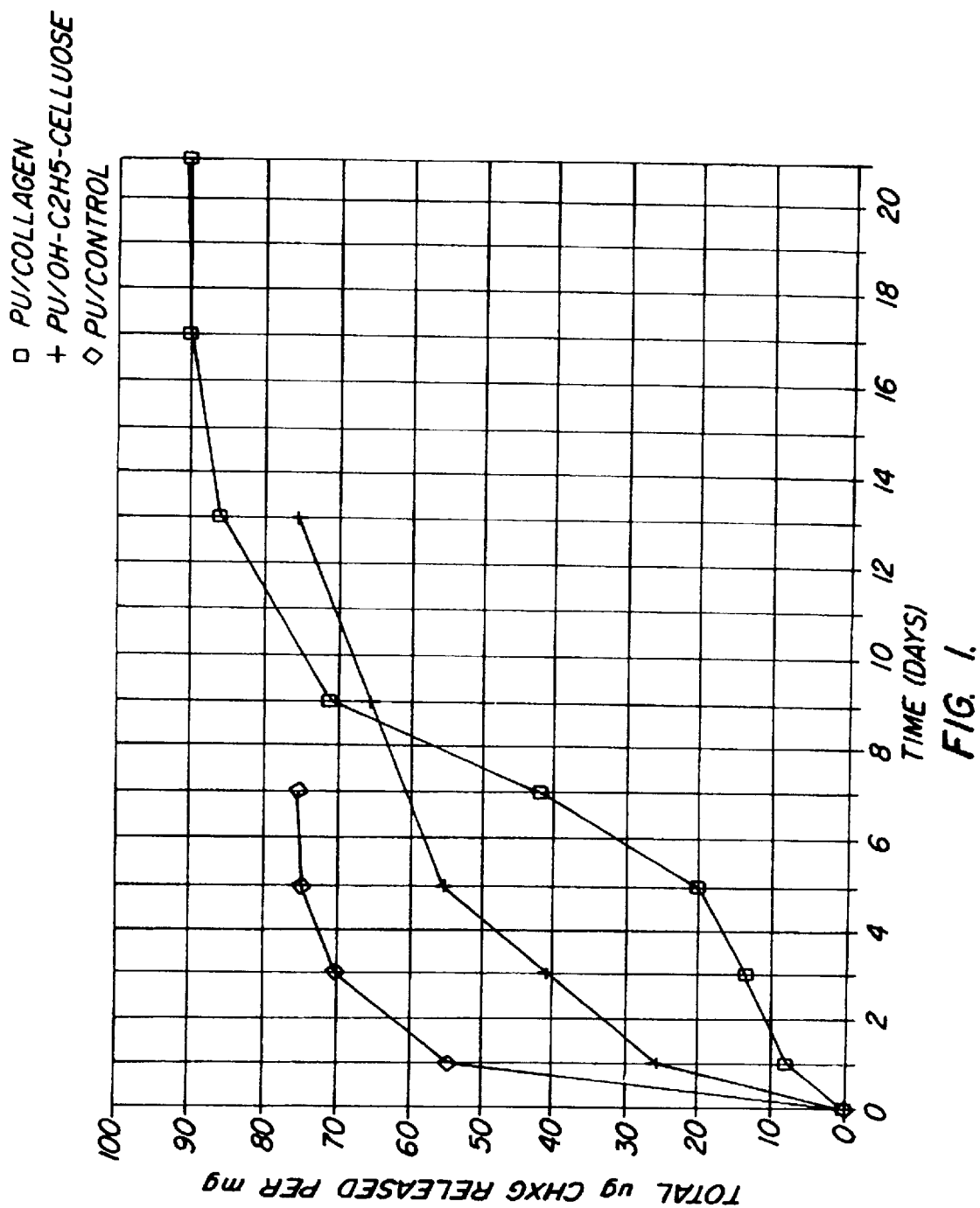
FIG. 1 is a graph of the weight of chlorhexidene gluconate released versus time from two types of polyurethane-modified biopolymers and from a polyurethane control polymer.

The polymeric delivery vehicle for controlled release of a bioactive agent according to the present invention may be formed by treating a biopolymer with a cross-linking agent whereby the cross-linking agent is simultaneously polymerized and formed into cross-linking moieties with the biopolymers. The preferred cross-linking agents are polyisocyanate-terminated polyurethane or polyurethane urea pre-polymers which are known in the art. If water is used as a solvent the reaction of the polyurethane or polyurethane urea cross-linking agent via the isocyanate side and/or end groups of the cross-linking agent is carbon dioxide which results in a foam material. If non-protic solvents are used, a solid (unfoamed) polymeric composite will result. A material may be cast into films, slabs or molded into desired shapes.

The biopolymers which are to be treated with a cross-linking agent according to the present invention include, but are not limited to proteins, peptides and polysaccharides, such as:

| Biopolymer | Biological Source |
|---|---|
| 1. Polygalacturonic acid | Citrus peels |
| 2. Hydroxypropyl celluose | Wood |

-continued

| Biopolymer | Biological Source |
|---|---|
| 3. Hydroxyethyl celluose | Wood |
| 4. Heparin | Porcine intestine |
| 5. Collagen | Animal tendon, hide |
| 6. Gelatin | Animal hide |
| 7. Carboxymethyl celluose | Wood |
| 8. Pectin | Citrus peels |
| 9. Algin | Kelp |
| 10. Ethyl celluose | Wood |
| 11. Glycosaminoglycan | Animal Tissues |
| 12. Chitin/Chitosan | Arthropods |
| 13. Other polysaccharides | — |

Preferred biopolymers are gelatin, collagen, and polysaccharides, particularly cellulose derivatives, as, for example, hydroxyethylcellulose.

The biopolymers which have a binding affinity above 0.8 with bioactive agents will typically have charged or highly polar groups in order to bind to bioactive agents containing highly polar or charged groups of the opposite charge from those on the biopolymer. Thus, the binding will occur by ionic interaction between the charged groups. Typical biopolymers containing charged groups are collagen, gelatin, hydroxyethylcellulose, and other polymers containing groups which can be charged, such as, $—N^+H_3$ and $—CO_2$, or which are highly polar, such as, —OH and —SH.

The thickness of the polymeric matrix may be varied as desired, depending upon the desired pharmaceutical dosage and duration of delivery. Ordinarily, a suitable matrix thickness will be in a range of about 0.1 to 1.0 centimeters.

The ratio of cross-linking agent to biopolymer will depend in part on the particular biopolymer and the bioactive agent with which it is intended to be used. It will be understood that mixtures of different biopolymers may also be utilized. However, generally, it will be useful to employ a weight ratio of cross-linking agent to biopolymer of from about 20:1 to about 1:1. It will be realized that suitable polymerization initiators may be utilized to initiate the polymerization reaction, which include, but are not limited to azobisisobutylnitrile, peroxide initiators, such as benzoyl peroxide, isopropyl peroxide, and the like. Although polyurethane and polyurethane ureas are the preferred cross-linking agents, other cross-linking agents may be suitable, such as alkylene polyacrylates, alkylene polymethacrylates, alkylene glycolpolymethacrylates, polyalkylene glycolpolymethacrylates, polyaldehydes as well as other cross-linking agents which will cross-link molecules with reactive protic groups. The cross-linking agents will have greater than two reactive sites/molecule, so the agents are statistically determined to be at least triacrylates, trialdehydes, and the like. The molecular weights of the cross-linking agents are also greater than about 500 (weight average), preferably greater than 1000. A preferred cross-linking agent is a polyether polyisocyanate sold as Hypol® Foamable Hydrophilic Prepolymer by W. R. Grace & Co. (Lexington, Mass.), which has greater than 2 free isocyanate groups/molecule. Unlike typical difunctional agents, cross-linking agents having greater than 2 reactive groups per molecule (a statistical average) can greatly affect crosslink density and enhance mechanical properties of the crosslinked material. The molecular weights are typically 1300–1400 (weight average).

It will be realized from the teachings herein that the degree of cross-linking, thickness and/or shape of the crosslinked biopolymer, and the degree of porosity (if any) are all parameters which may be controlled to attain a desired release profile of the bioactive agent from the cross-linked biopolymer. Furthermore, the biopolymer may be chemically modified to change its binding affinity for a selected bioactive agent. For example, hydroxyethyl cellulose may be partially methylated to reduce the number of cross-linking sites and/or potential chelating sites, depending upon whether the cross-linking is performed before or after the bioactive agent is impregnated into the biopolymer.

The shape of the cross-linked biopolymer may be formed by molding or casting before cross-linking or, after cross-linking, it may be formed into a desired shape by cutting. The cross-linked biopolymer will then be loaded with the desired bioactive agent(s), which is believed to occur by ionic binding involving ionic sites on the biopolymer, with the desired bioactive agent, which may be antimicrobial drugs or macromolecules such as growth factors, antibacterial agents, antispasmodic agents, or any other active biological bioactive agent, such as adrenergic agents such as ephedrine, desoxyephedrine, phenylephrine, epinephrine and the like, cholinergic agents such as physostigmine, neostigmine and the like, antispasmodic agents such as atropine, methantheline, papaverine and the like, tranquilizers and muscle relaxants such as fluphenazine, chlorpromazine, triflupromazine, mephenesin, meprobamate and the like, antidepressants like amitriptyline, nortriptyline, and the like, antihistamines such as diphenhydramine, dimenhydrinate, tripelennamine, perphenazine, chlorprophenazine, chlorprophenpyradimine and the like, hyptotensive agents such as rauwolfia, reserpine and the like, cardioactive agents such as bendroflumethiazide, flumethiazide, chlorothiazide, aminotrate, propranolol, nadolol, procainamide and the like, angiotensin converting enzyme inhibitors such as captopril and enalapril, bronchodilators such as theophylline, steroids such as testosterone, prednisolone, and the like, antibacterial agents, e.g., sulfonamides such as sulfadiazine, sulfamerazine, sulfamethazine, sulfisoxazole and the like, antimalarials such as chloroquine and the like, antibiotics such as the tetracyclines, nystatin, streptomycin, cephradine and other cephalosporins, penicillin, semi-synthetic penicillins, griseofulvin and the like, sedatives such as chloral hydrate, phenobarbital and other barbiturates, glutethimide, antitubercular agents such as isoniazid and the like, analgesics such as aspirin, acetaminophen, phenylbutazone, propoxyphene, methadone, meperidine and the like, etc. These substances are frequently employed either as the free compound or in a salt form, e.g., acid addition salts, basic salts like alkali metal salts, etc. Other therapeutic agents having the same or different physiological activity can also be employed in the pharmaceutical preparations within the scope of the present invention. Typically, the bioactive agent dissolved in a suitable solvent will be contacted with the cross-linked biological polymer by immersion. The loading of the biopolymer may be readily determined based upon the uptake of the biopolymer of the bioactive agent.

In a preferred method for forming the loaded cross-linked biopolymer, the bioactive agent is dissolved in water at a suitable concentration, typically about 1–2% by weight, and the cross-linked biological polymer is immersed therein for a period of about 240 minutes. At ambient temperature (about 20–25° C.), the biopolymer is then extracted from the solvent, allowed to air dry or is lyophilized, and is then ready for use.

Alternatively, the cross-linked biopolymer may be loaded with the bioactive agent, then dried, then cut to a suitable form for use.

In another preferred method, the bioactive agent and biopolymer are dissolved in an aqueous solvent before cross-linking and the bioactive agent is bound to the biopolymer. Typical agent: biopolymer weight ratios are in the range of about 1:100 to 5:100 in solution. The biopolymer is then cross-linked by treatment with the cross-linking agent.

It will be realized that the biopolymer material may be modified, for example, so as to be made more hydrophilic or hydrophobic to adjust for suitable binding properties to the bioactive agent. Such modification may be performed by, for example, esterification of acid groups in the biopolymer prior to cross-linking, thus making the biopolymer more hydrophobic.

The general reactions for a typical treatment of a biopolymer having protic groups (-HX) with polyisocyanate are shown below in Table 1.

TABLE 1

General reaction of polyisocyanate with acidic group $$O{=}C{=}N{-}R{-}N{=}C{=}O + {-}XH$$

$$\underset{X\ =\ {-}CO_2,\ {-}S,\ {-}O,\ {-}N}{{-}X{-}\overset{O}{\underset{\|}{C}}{-}NH{-}R{-}NH{-}\overset{O}{\underset{\|}{C}}{-}X{-}}$$

Polyurethane prepolymer

Polyether Polyisocyanate

FOAMING:

- $RNCO + H_2O \longrightarrow RN\overset{O}{\underset{\|}{H}COH}$  Unstable Carbamic Acid

- $RN\overset{O}{\underset{\|}{H}COH} \longrightarrow RNH_2 + CO_2\uparrow$  Amine Formation, Gas Generation

- $RNH_2 + RNCO \longrightarrow RN\overset{O}{\underset{\|}{H}CNHR}$  Urea Chain Extension, Cross-Linking Formation Referring to the Figures, in FIG. 1 there is shown a graph of drug release of chlorhexidene gluconate from two biopolymers as compared to a contrast polymer. The control polymer is polyurethane (PU). One of the test foams is polyurethane cross-linked (10 wt. %) collagen and polyurethane cross-linked (10 wt. %) hydroxyethyl celluose (HEC). The foams and control were soaked in a 2% solution of chlorhexidine gluconate (CHXG) for the same period of time. To measure the drug efflux from each of the biopolymers, each was placed in a large reservoir of physiological saline and the bathing medium was changed daily to maintain sink conditions. As shown in FIG. 1, the drug was released quickly and completely from the control foam by the fifth day. A more controlled release was achieved in the cross-linked hydroxyethyl celluose, with the drug still being slowly released after 13 days. Release from HEC can extend beyond 13 days, but in that test the experiment was stopped after 13 days. A more extended release profile is shown in the cross-linked collagen, with drug release occurring even up to 17 days, when the experiment was stopped. Moreover, it can be seen from the graph that a greater amount of CHXG was released from the two test samples than from the control. Although the HEC test was halted after 13 days, its CHXG release curve was still on an upward slope, and it already had released about as much CHXG as the control.

Figure 2:
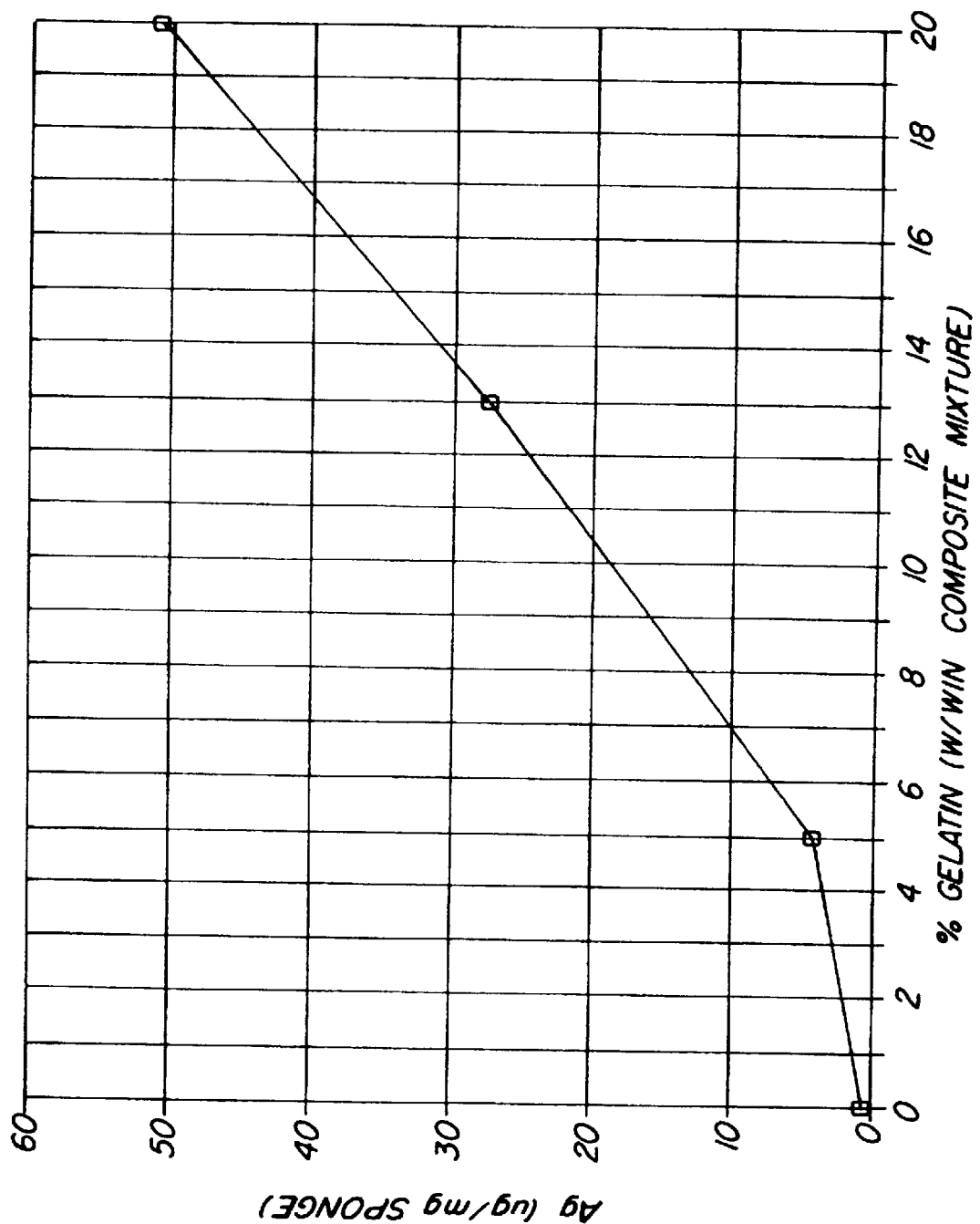
FIG. 2 is a graph of drug loading (silver ion) as a function of amount of biopolymer (gelatin) in a gelatin-polyurethane composite sponge.

In FIG. 2 there is shown a graph of drug loading, where the drug is a silver ion, as a function of the amount of gelatin (biopolymer) in a gelatin-polyurethane composite sponge. It can be seen that without the biopolymer (0% gelatin) there is essentially no binding taking place whereas the drug binding increases with increasing amount of biopolymer present in the composite.

Figure 3:
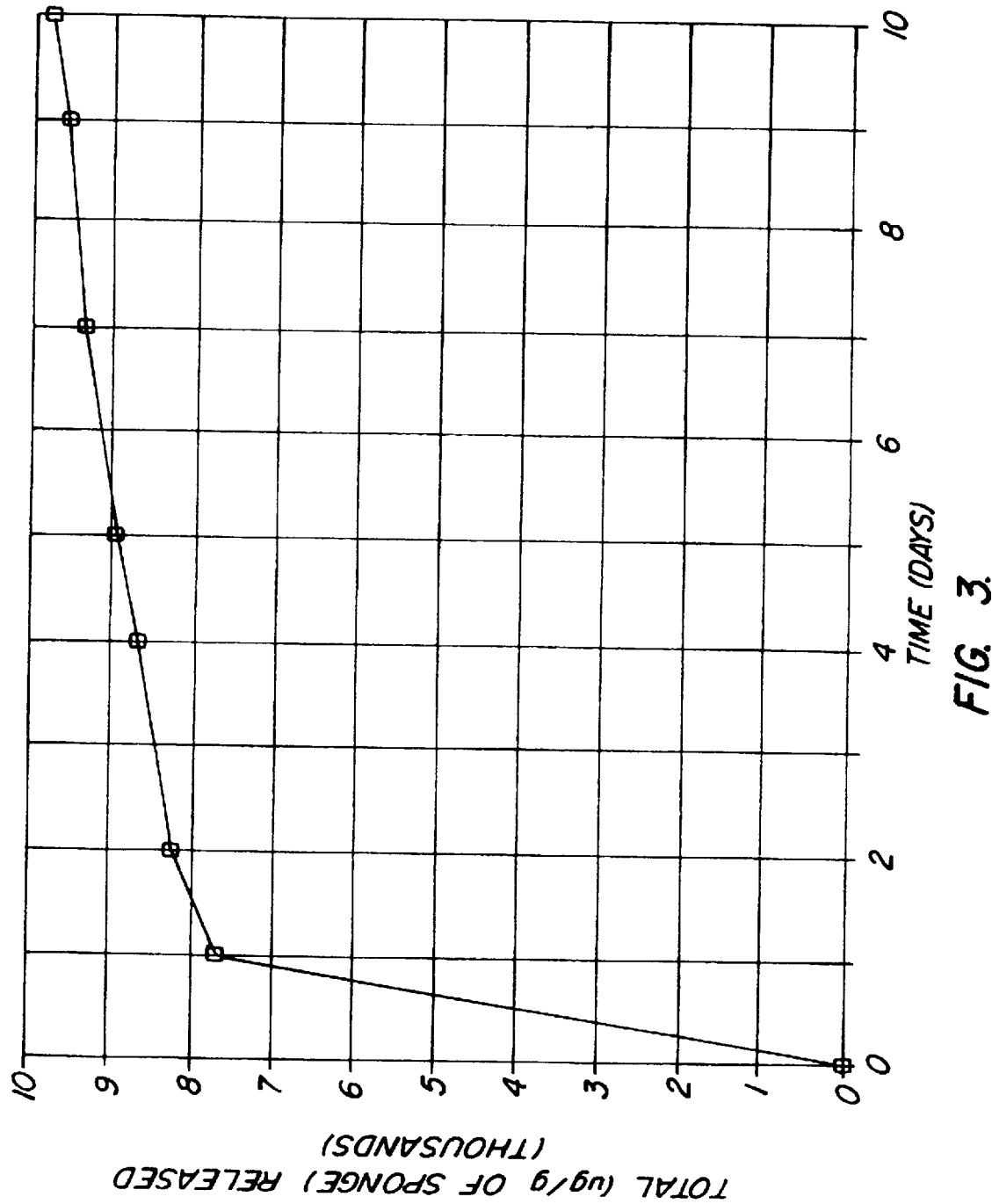
FIG. 3 is a graph of a typical drug (silver ion) release rate from a composite of polyurethane - 22% gelatin.

Referring to FIG. 3 there is shown a graph of a chemical drug release rate (of silver ion) from a composite of polyurethane —22% gelatin. It can be seen that there is a surge of drug release during the first day, then in the second day, continuing to the tenth day (the end of the particular test) there is a relatively constant rate of release of the drug from the composite.

Figure 4:
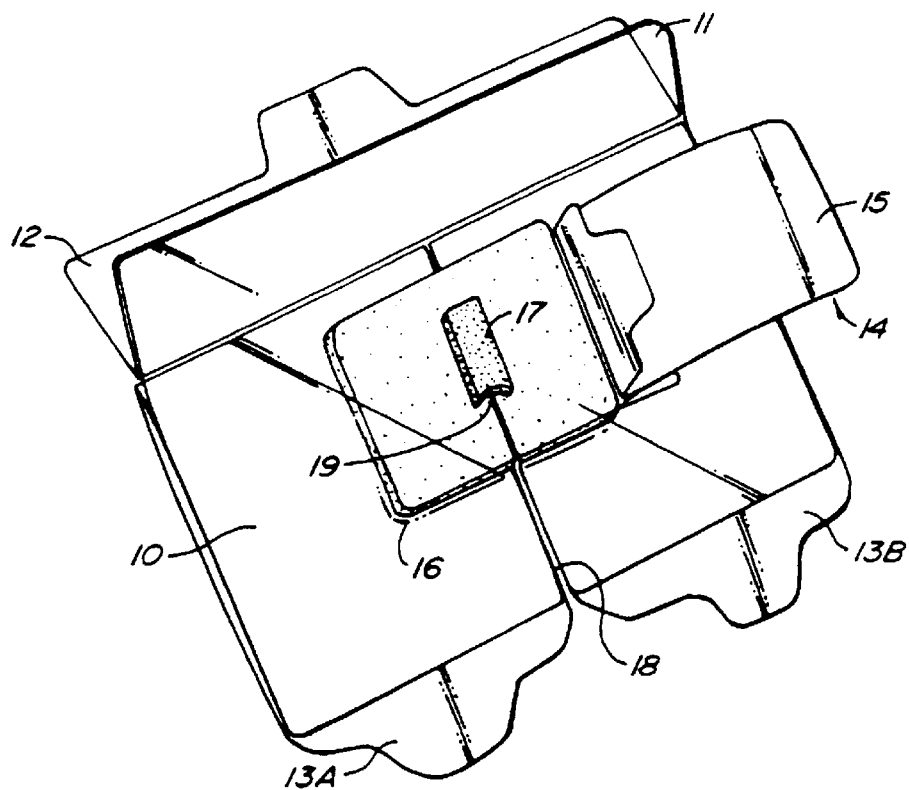
FIG. 4 is a perspective view of a preferred embodiment of a catheter-securing and drug delivery device according to the present invention.

Referring to FIG. 4, there is shown a preferred embodiment of the present invention in a catheter-securing and drug delivery device. The device comprises a reinforced, flexible, water vapor permeable membrane 10, a portion of which is upturned as a flap 11. Membrane 10 may be made of any water vapor permeable synthetic polymer such as a polyurethane or polyester reinforced with thread. At least the edges of the bottom surface of membrane 10 (including flap 11) are coated with an adhesive (not shown). Alternatively, the entire bottom surface of membrane 10 (including flap 11) may be coated with an adhesive. On the bottom surface of the membrane 10, about centrally located thereunder, is affixed an elastomeric pad 16. The elastomeric pad 16 will be a cross-linked, biological polymer loaded with a bioactive agent modified according to the present invention. Preferably, the biopolymer comprises a cross-linked hydroxyethyl cellulose and the bioactive agent is an antimicrobial agent such as chlorhexidene gluconate. Both the membrane 10 and the pad 16 are adapted with slit 18, with the slit in pad 16 being collinear with the slit in the membrane 10. Both slits terminate at a point 19 located proximate to the center of the pad 16. At point 19 the pad 16 and membrane 10 will surround a catheter (not shown) whereby the membrane 10 and pad 16 serve as a catheter fixing device. The pad 16 additionally serves as a drug delivery component for delivering antimicrobial agents or other agents to the wound caused by the catheter. Thus, pad 16 may be used without membrane 10, in an alternative embodiment, in which case at least the edges of the bottom surface of pad 16 will be coated, impregnated, or otherwise adapted with an adhesive material.

Returning to FIG. 4, on the upper surface of the membrane 10 and adjacent to the central point 19 is shown an optional pillow 17 which, may also be made of a crosslinked biological polymer loaded with an antimicrobial agent according to the present invention. The purpose of the pillow 17 is for receiving and supporting the side of the catheter (not shown), since catheters may extend from the skin surface at an oblique angle. The extension of the catheter from the skin may be rested upon the pillow 17. Adjacent to the slit 18 is flap 14 which may be made of the same reinforced, flexible, water vapor permeable material as membrane 10 and is affixed to membrane 10. The flap 14 is shown in an open position, therefore the reinforced, flexible, water vapor permeable membrane is on the underside and not seen in the Figure. The flap 14 is coated with an adhesive (not shown) and the adhesive is protected by a removable protecting layer (such as, paper or plastic) 15. Once the catheter is in place at central port 19 the flap 14 is folded over the catheter and, by removal of layer 15, the flap 14 is adhesively attached over a portion of the slit 18, the pillow 17, a portion of the catheter (not shown) as well as over a portion of the upper surface of the membrane 10. This serves not only to affix the catheter but also to maintain the slit 18 in a closed position.

In an alternative embodiment, still referring to FIG. 4, the device may be used as a wound dressing for use with percutaneous catheters without the catheter-securing feature of flap 14 (and protecting layer 15) by assembling the device without these items. Without flap 14, the pillow 17 may also be optionally deleted.

Before use, the bottom adhesively coated surfaces of membrane 10 (including flap 11) are protected, as shown, by three removable layers 12, 13a, 13b (made, for example, of paper or plastic). First, layer 12 is removed and the catheter is pulled through slit 18 until it is engaged at central point 19. The adhesive portion of flap 11 is then secured to the skin. Then layers 13a and 13b are removed and the remainder of the membrane 10 is secured to the skin. Finally, the catheter is securely placed onto pillow 17 (if present) and flap 14 is folded over, and, after removal of layer 15, flap 14 is secured over the catheter and membrane 10.

A particular advantage of the device shown in FIG. 4 is that it is light, easily used and disposable, as opposed to other catheter-securing devices which accommodate complex mechanical parts, some of which must be sterilized for re-use. Another advantage of the device shown in FIG. 4, particularly when used in conjunction with the cross-linked biopolymer according to the present invention, is that it can administer at the wound site of the catheter not only an antimicrobial agent, but also growth factors or other desirable bioactive agents which would assist not only in combating infection, but also in healing of the wound. If desired, an immune-modulating factor may also be incorporated into the device for those patients who may have allergic reaction to the bioactive agent.

Figure 5:
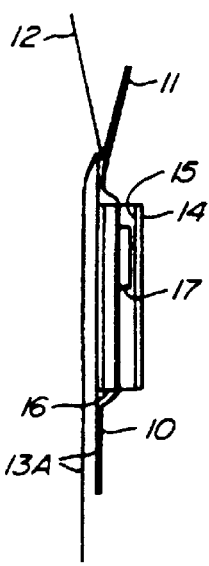
FIG. 5 is a side view of the device shown in FIG. 4.

Referring to FIG. 5 there is shown a side view of the device shown in FIG. 4. As can be seen in FIG. 5, the removable layer 13a (as well as 13B) is actually folded over onto itself so that when it is pulled in a downward direction (as shown in FIG. 5) it can be pulled away without changing the positioning of the device.

Figure 6:
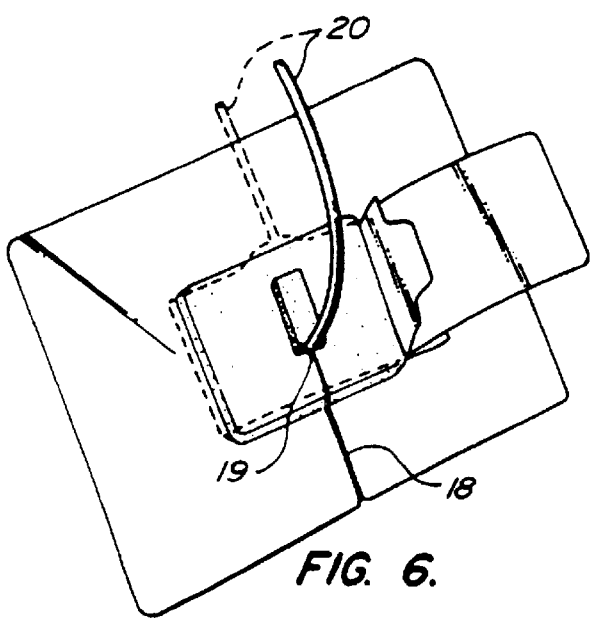
FIG. 6 is a perspective view of a catheter-securing device accommodating a catheter.

Referring to FIG. 6 there is shown the device of FIG. 4 accommodating a catheter 20 which has been inserted into central point 19 by slipping through slit 18.

Figure 7:
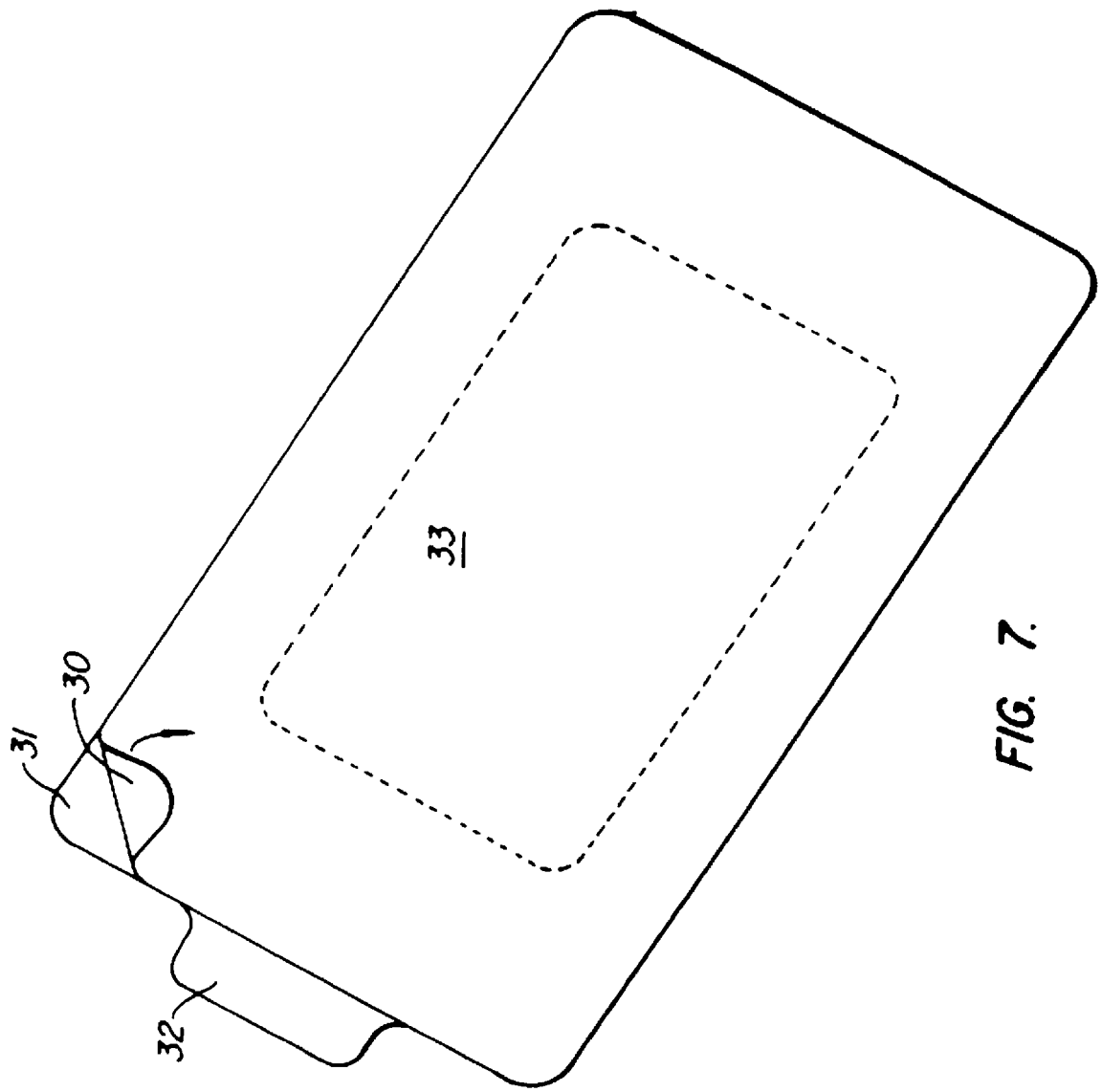
FIG. 7 is a plan view of a wound dressing according to the present invention.

Referring to FIG. 7 there is shown a wound dressing comprising a flexible moisture permeable membrane 30 having an adhesive surface protected by a removable layer 31, a portion 32 of which extends beyond the membrane 30 for convenience. Approximately centrally located on the underside of membrane 30 is an elastomeric pad 33 made of a material according to the present invention (preferably, a biopolymer-polyurethane containing an antimicrobial agent)

which is to be placed in direct contact with the wound. This dressing may also be utilized as a drug delivery device, particularly to deliver antimicrobial agents and wound-healing agents. An immune-modulating factor may also be used if the patient exhibits an allergic reaction to the antimicrobial agent.

The following examples are presented for the purpose of illustration and are not intended to limit the invention in any way.

EXAMPLE 1

To a 2.5% (w/v) solution of hydroxyethylcellulose is added (1:1 weight ratio) anhydrous polyisocyanate-terminated urethane pre-polymer. The mixed composite is placed in an open vessel, and cured for about 30 minutes at R. T. to form a "bun". The bun is cut into a desired shape and placed in a 2.5% (v/v) solution of 22% chlorhexidine gluconate (adjusted at pH 8.0 with ammonium hydroxide). After incubation for 4 hours, the sponge is removed, frozen and lyophilized.

EXAMPLE 2

In an aqueous solution of gelatin (120 g/100 ml water), adjusted to pH 7.6, is added silver nitrate to the desired silver ion concentration, and the mixture is stirred for at least 4 hours in a brown glass bottle. The pH is adjusted to 7.2 and stirring is continued for 2 hours. The 36 parts of anhydrous polyisocyanate-terminated urethane prepolymer is added per 64 parts of the gelatin-silver solution. The mixture is placed in an open vessel and allowed to cure for 30–45 minutes at R.T. to form a bun. The bun is cut into desired shapes and washed in deionized water.

EXAMPLE 3

DETERMINATION OF DRUG BINDING TO BIOPOLYMER

Figure 8:
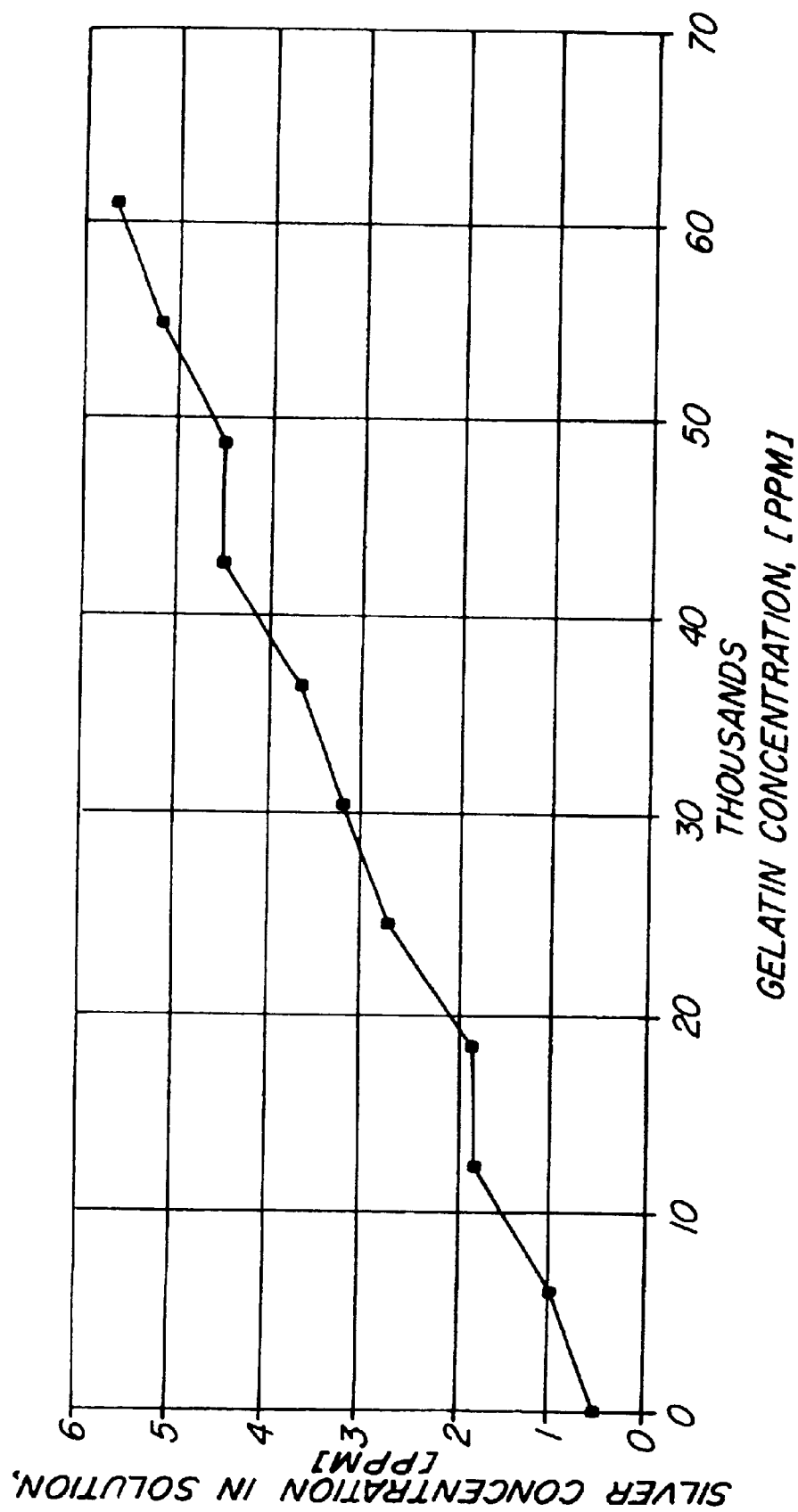
FIG. 8 is a graph of silver ion concentration versus gelatin concentration found according to the test in Example 3.

Saturated solutions of silver carbonate at pH 7 were prepared with varying levels of gelatin. The silver in solution was measured for the samples to determine the binding constant for silver to gelatin under these conditions. FIG. 8 is a graphical representation of the results, demonstrating that gelatin appreciably binds silver ion, increasing the solution concentration of silver. Due to its ability to bind silver ions, gelatin is a good candidate as the biopolymer component of a polymer composite to provide sustained release of silver.

EXAMPLE 4

DETERMINATION OF DRUG BINDING TO BIOPOLYMER COMPOSITE

Polyurethane-gelatin composite sponges of varying gelatin content were prepared by reacting aqueous solutions of gelatin of varying concentration with a standard amount of an anhydrous polyether, polyisocyanate terminated prepolymer (HYPOL® FHP 2002). The resultant sponges were washed, dried, and placed into a dilute solution of silver nitrate. The amount of fluid absorbed into the sponge, the silver concentration of the sponge, and the silver concentration of the surrounding solution in equilibrium with the sponge were measured. From the wet weight of the sponge, the passive drug absorption of the sponge due to the fluid content can be calculated. The amount of silver in the sponge in excess of that due to passive fluid absorption is due to active binding of silver ions:

Bound Drug =[Total Drug in Sample]-[Fluid Content * Solution Concentration]

A method of expressing the drug affinity of a material is by the ratio of "bound drug" to "free drug":

Bound Drug/Free Drug =Bound Drug/[Total Drug— Bound Drug]

Figure 9:
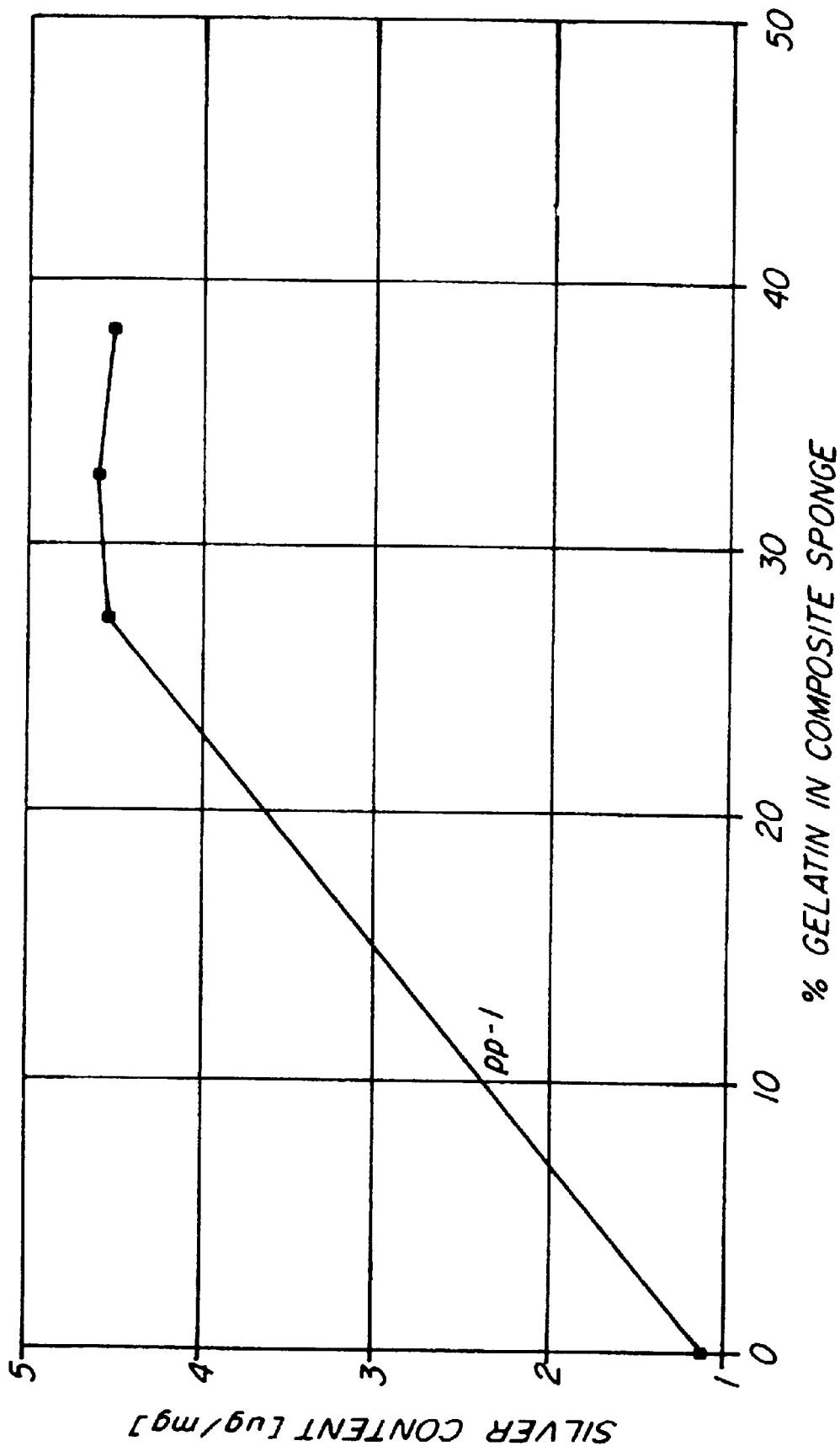
FIG. 9 is a graph of silver ion content in cross-linked polyurethane/gelatin sponges v. gelatin content found according to the test in Example 4.
Figure 10:
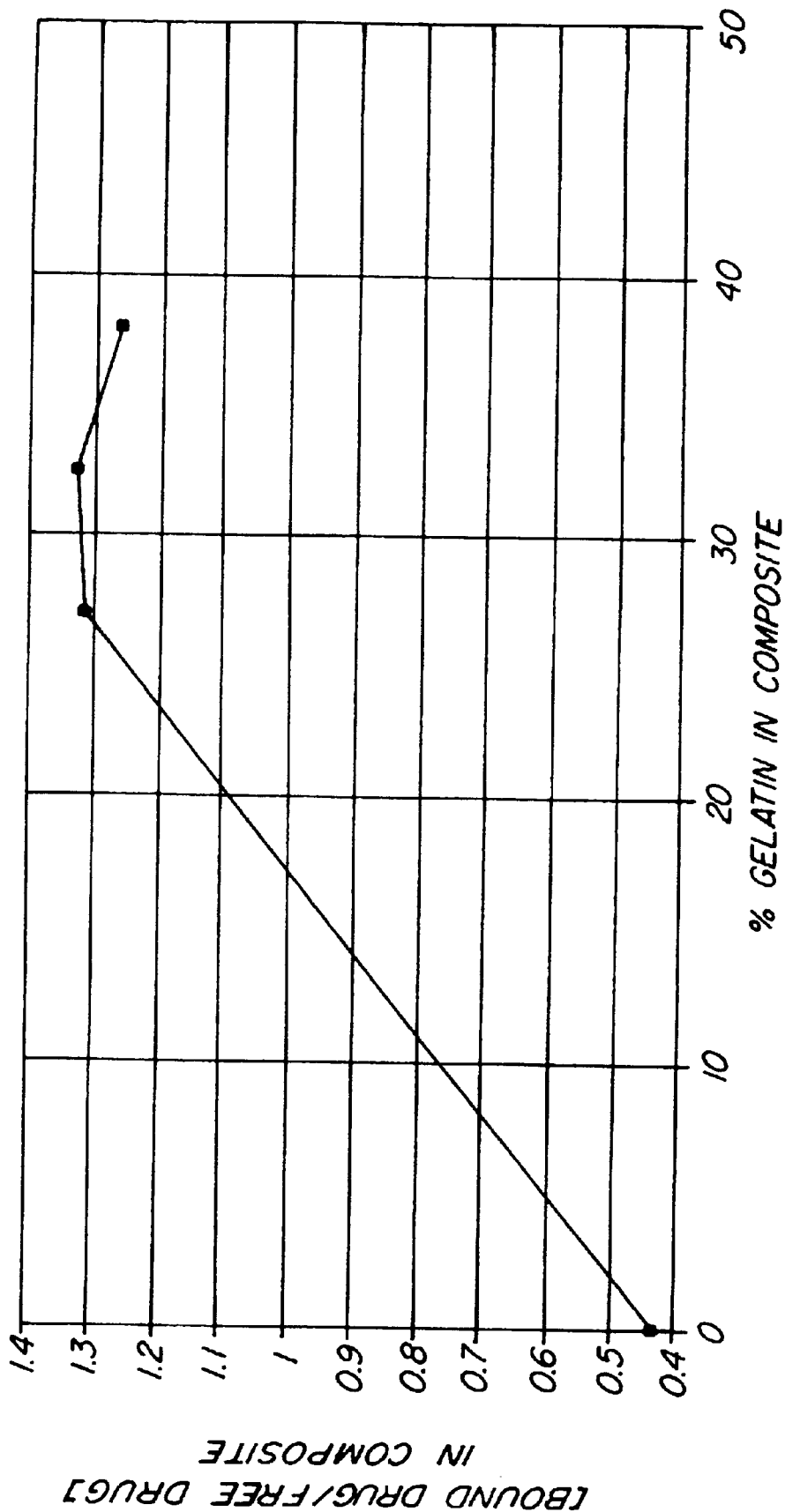
FIG. 10 is a graph of drug affinity in cross-linked polyurethane/gelatin sponges v. gelatin content found according to the test in Example 4.

Due to the increased drug affinity for the polymer of the drug reservoir a higher Bound/Free ratio provides greater sustained release of drug. FIGS. 9 and 10 describe the results of silver binding to the composite sponges of Example 9. It is readily evident that the gelatin component greatly increases the total amount of drug bound to the composite material (FIG. 9), thereby creating a drug reservoir. The gelatin component also increases the Bound/Free ratio (FIG. 10), providing the drug affinity for sustained drug release instead of undesired rapid drug "dumping".

The foregoing description and examples have been set forth merely to illustrate the invention and are not intended to be limiting. Since modifications of the described embodiments incorporating the spirit and substance of the invention may occur to persons skilled in the art, the scope of the invention is to be limited solely with respect to the appended claims and equivalents.

What is claimed is:

1. A method for preparing a polymeric delivery vehicle for controlled-release of a bioactive agent comprising the steps of:

treating with a cross-linking agent a biopolymer containing chemically reactive functionalities which react with said cross-linking agent, wherein said cross-linking agent comprises greater than two reactive sites per molecule which are chemically reactive with said functionalities, to form a cross-linked biopolymer;

wherein said treating step is conducted in the presence of a protic solvent whereby a gaseous side product is evolved, whereby said cross-linked biopolymer is formed as a foam;

optionally, forming said cross-linked biopolymer into a desired shape;

contacting said cross-linked biopolymer with a solution containing said bioactive agent to noncovalently bind at least a portion of said bioactive agent to said cross-linked biopolymer to form said polymeric delivery vehicle, wherein the rate of release of said bioactive agent is controlled by the binding affinity of said cross-linked biopolymer with said bioactive agent, and wherein said binding affinity is above 0.8.

2. A method for preparing a polymeric delivery vehicle for controlled-release of a bioactive agent comprising the steps of:

contacting a biopolymer containing chemically reactive functionalities which react with a cross-linking agent with a solution containing a bioactive agent to noncovalently bind at least a portion of said bioactive agent to said polymer;

optionally, forming said biopolymer into a desired shape; and treating said biopolymer with a cross-linking agent wherein said cross-linking agent comprises greater than two reactive sites per molecule which are chemically reactive with said functionalities, to form said polymeric delivery vehicle, wherein the rate of release of said bioactive agent is controlled by the binding affinity of said cross-linked biopolymer with said bioactive agent, and wherein said binding affinity is above 0.8, wherein said treating step is conducted in the presence of a protic solvent whereby a gaseous side product is evolved, whereby said cross-linked biopolymer is formed as a foam.

3. A method according to claim 1 or 2 wherein said cross-linking agent is selected from the group consisting essentially of polyurethanes and polyurethane ureas having isocyanate side groups and/or end groups.

4. A method according to claim 1 or 2 wherein the molecular weight of said cross-linking agent is greater than 500.

5. A method according to claim 4 wherein said molecular weight is greater than 1000.

6. A method according to claim 1 or 2 wherein said binding affinity is 1.0 or higher.

7. A method according to claim 6 wherein said binding affinity is in the range of 1.0 to 5.0.

8. A method according to claim 1 or 2 wherein said step of forming said cross-linked biopolymer into a desired shape is performed by molding.

9. A method according to claim 1 or 2 wherein said biopolymer is selected from the group consisting of gelatin, collagen, and polysaccharides.

10. A method according to claim 1 or 2 wherein said biopolymer comprises charged groups and said bioactive agent comprises charged groups whereby there is binding of said agent and said biopolymer by ionic interaction of said charged groups.

11. A method according to claim 1 or 2 wherein said bioactive agent comprises chlorhexidine.

12. A method according to claim 9 wherein said polysaccharide is a cellulose derivative or glycosaminoglycan.

13. A method according to claim 1 or 2 wherein said biopolymer is selected from the group consisting of a protein and peptide.

14. A method according to claim 13 wherein said biopolymer further comprises silver ions chelated to said protein or peptide.

15. A method according to claim 1 or 2 wherein said bioactive agent comprises an anti-microbial agent.

16. A method according to claim 1 or 2 wherein said bioactive agent comprises a pharmacological drug.

17. A method according to claim 1 or 2 wherein said bioactive agent comprises a growth factor.

* * * * *